United States Patent [19]

Bacchi et al.

[11] Patent Number: 4,914,086
[45] Date of Patent: Apr. 3, 1990

[54] METHOD FOR TREATING AFRICAN HUMAN AND VETERINARY TRYPANOSOMIASES

[75] Inventors: Cyrus J. Bacchi, East Northport, N.Y.; Randolph L. Berens, Littleton; J. Joseph Marr, Englewood, both of Colo.; Henry C. Nathan, Riverdale, N.Y.

[73] Assignees: University Patents, Inc.; Pace University

[21] Appl. No.: 134,931

[22] Filed: Dec. 18, 1987

[51] Int. Cl.⁴ ............................................. A61K 31/70
[52] U.S. Cl. ........................................................ 514/45
[58] Field of Search ................................... 514/45-46

[56] References Cited

FOREIGN PATENT DOCUMENTS 2548190 1/1985 France .................................. 514/46

OTHER PUBLICATIONS

McCabe et al., The Chemical Abstracts, 102: 197595b (1985).
Bacchi et al., The Chemical Abstracts, 107: 168425m (1987).
Berman et al., The Chemical Abstracts, 106: 95635e (1986).
Marr et al., The Chemical Abstracts, 107: 150632e (1984).
Zweygarth et al., The Chemical Abstracts, 106: 43506u (1987).
Bacchi et al., "Parasitic Protozoa and Polyamines", Academic Press, 1987.
Bacchi et al., Am. J. Trop. Med. Hyg., 36(1), pp. 46–52 (1987).
Marr et al., Antimicrobial Agents and Chemotherapy, pp. 292–295 (1984).
Bacchi et al., Antimicrobial Agents and Chemotherapy, pp. 1406–1413 (1987).
Fish et al., Antimicrobial Agents and Chemotherapy, 27, No. 1, 33–36 (1985).
Schechter et al., Parasitolog Today, vol. 2, No. 8 (1986).

*Primary Examiner*—John W. Rollins
*Attorney, Agent, or Firm*—Handal & Morofsky

[57] ABSTRACT

Purine analogs sinefungin, formycin B and 9-deazainosine or its pharmaceutically aceptable acid addition salts are usful in treating African human and veterinary trypanosomiases.

4 Claims, No Drawings

METHOD FOR TREATING AFRICAN HUMAN AND VETERINARY TRYPANOSOMIASES

FIELD OF INVENTION

The invention relates to a method for treating *Trypanosoma brucei brucei* infections, the causative agent for African human and veterinary trypanosomiases which employs the purine analogs 6,9-Diamino-1-(6-amino-9H-purin-9-yl)-1,5,6,7,8,9-hexadeoxy-beta-D-ribo-decofuranuronic acid (sinefungin), 7-hydroxypyrazolo (4, 3-d) pyrimidine ribonucleoside (formycin B), and 7-beta-D-ribofuranosyl-4-oxo-3H, 5H-pyrrolo (3, 2-d) pyrimidine (9-deazainosine) or its pharmaceutically acceptable acid addition salt thereof.

BACKGROUND OF THE INVENTION

The purine analogs with which the present invention is concerned has the following structural formula I and Ia.

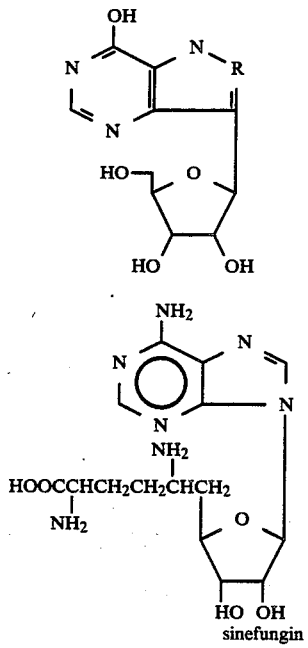

wherein
R=C is 9-deazainosine (9-DINO) and
R=N is formycin B.

The synthesis of the above analogs and the disclosure of their antitumor and antiprotozoal activities are described in the following publications.

1. R. Klein, et al., *Tetrahedron Letters*, 21, 1013–1016, (1980).
2. Mee-ILL Lim, et al., *Journal of Organic Chemistry*, 48, 780–788, (1983).
3. J. Joseph Marr, et al., *Antimicrobial Agents and Chemotherapy*, 25, 292–295 (1984).
4. J. Joseph Marr, et al., *Antimicrobial Agents and Chemotherapy*, 27, 33–36, (1985).
5. J. Joseph Marr, et al., *Antimicrobial Agents and Chemotherapy*, 30, 1981–183, (1986).

The above publications numbered 1 and 2, namely *Tetrahedron Letters* and the *Journal of Organic Chemistry*, describe the synthesis of the purine analogs, of forumula I of the present invention and their use as antitumor agents.

J. Joseph Marr, et al., *Antimicrobial Agents and Chemotherapy*, 25, 292–295, (1984), describes the activities of six purine analogs, namely, 7-deazainosine, 9-deazainosine, allopurinol riboside, formycin B, 8-azainosine and 7-thia 7,9-dideazainosine against the three protozoan pathogens Leishmania donovani, Trypanosoma cruzi, and Trypanosoma gambiense.

The two latter pathogens include American as well as African trypanosomes. All these six analogs were active against the above three pathogens in tissue culture systems that is in vitro.

J. Joseph Marr, et al., *Antimicrobial Agents and Chemotherapy*, 27, 33–36, (1985), also describes six purine analogs, which are allopurionol, allopurinol ribonucleoside, thiopurinol, thiopurinol ribonucleoside, formycin B and 9-deazainosine and their activity against Trypanosoma brucei gambiense, and Trypanosoma brucei rhodesiense in cell cultures that is in vitro and in vivo against bloodstream forms grown in a bone marrow tissue culture system. The two carbon-nucleosides, namely, formycin B and 9-deazainosine were found to be active at very low concentrations with formycin B somewhat more efficacious than 9-deazainosine in the bone marrow tissue culture system.

Finally, the last publication, J. Joseph Marr et al., *Antimicrobial Agents and Chemotherapy*, 30, 181–183, (1986), describes three analogs of inosine, formycin B, allopurinol ribonucleoside, and 9-deazainosine and their activities against Pneumocystis Carinii in tissue culture system. The two analogs formycin B and 9-deazainosine were active in this tissue culture system. The organism Pneumocystis Carinii causes pneumonia in humans.

The present invention can be distinguished from the above prior art in that it is directed to a use which is unexpected and which can be distinguished from its application in the above-described tissue culture system. Usefulness in any of the above systems would not suggest or in any way make obvious the use of the purine analogs of formula I and Ia of the present invention in *Trypanosoma brucei brucei* infections, which causes African human and veterinary trypanosomiases that is sleeping sickness.

Treatment of African trypanosomiasis has a long history dating back to 1905 with the discovery of phenyl-arsenical atoxyl. Since that time, the control of human African sleeping sickness has rested on two additional arsenicals, one naphthylamine sulfonic acid and one diamidine, all discovered before 1950. These compounds have severe toxicity problems and therefore, present safety problems. A list of compounds and their combinations which are currently used for the treatment of this disease is found in Chapter 5, pages 129–136, entitled "Protozoan Infections of Man African Trypanosomiasis" in *Chemotherapy of Parasitic Diseass*, Editors William C. Campbell and Robert S. Rew, Publisher Plenum Press, 1986.

However because of the toxicities of these compounds and their combinations, no safe effective treatment for this disease in man is presently available.

In summary, there exists nothing in the prior art that would teach or suggest that purine analogs of formula I and Ia of the present invention and their pharmaceutically acceptable salts would be useful for treating African human and veterinary trypanosomiases. The purine analogs and their pharmaceutically acceptable salts of the present invention can be surprisingly used to treat this disease with little or no toxicity to the human being or an animal.

SUMMARY OF THE INVENTION

The method of the present invention is intended for treating African human and veterinary trypanosomiases caused by *Trypanosomia brucei brucei*. The method essentially involves administration of sinefungin, formycin B or 9-deazainosine or its pharmaceutically acceptable acid addition salt thereof to a human being or an animal in need of such treatment. For use in the instant method, oral or parenteral administration of sinefungin, formycin B or 9-deazainosine or its pharmaceutically acceptable acid addition salt thereof is anticipated as being the preferred route. The preferred analogs of the present method are formycin B and 9-deazainosine because of their greatest activity. The most preferred analog is 9-deazainosine on account of its being highly effective.

DETAILED DESCRIPTION OF THE INVENTION

The purine analogs of formula I and Ia of the present invention were tested for their effectiveness in curing acute and central nervous system infections in vivo in murine models (mice) of *Trypanosoma brucei brucei*. Two additional purine analogs namely, allopurinol and allopurinol riboside were also tested in the same animal models as comparative compounds. These animal models are the accepted standard in this art and the effectiveness of the purine analogs in these models indicate that these analogs will also be effective in a human being or an animal infected by *Trypanosoma brucei brucei*. The effectiveness of the purine analogs of the present invention in said murine models is shown in Table 1, 2, 3, 4, and 5 given in the Example 1. As can be seen from said tables 1, 2, 3, 4 and 5, the analogs with the greatest activity were formycin B and 9-deazainosine. The most active analog of the two is 9-deazainosine (9-DINO).

The method of the present invention essentially involves administration of a non-toxic effective amount of sinefungin, formycin B or its pharmaceutically acceptable salt thereof to a human being or an animal suffering from African trypanosomiases which is caused by the parasite *Trypanosomia brucei brucei*. The African trypanosomiases is commonly known as sleeping sickness.

The most preferred method of the present invention involves administration of a non-toxic effective amount of 9-deazainosine or its pharmaceutically acceptable salt to a human being or an animal suffering from African sleeping sickness.

It should be noted that the effective amount of the purine analogs of formula I and Ia and their dosage, will depend on the specific species, the age of the animal and the human being.

Any mineral acids are basically useful as acids for forming pharmaceutically acceptable salts. Such acids are for example, hydrochloric acid, sulfuric acid, phosphoric acid and other acids commonly used in the pharmaceutical industry. Preparation of these salts is carried out by conventional techniques.

Administration of the purine analogs of the present invention may be made by the parenteral, oral, sublingual, or rectal route as well as by nasal or dermal application. The oral and parenteral route is preferred, however.

Thus, the purine analogs of the present invention may be formulated for parenteral use in a conventional manner utilizing known pharmaceutical carriers and excipients and may be presented in unit dosagae form or in multi-dosage containers. The composition may be in the form of solutions, suspensions or emulsions in oily or aqueous vehicles and may contain conventional dispersing, suspending or stabilizing agents. The composition may also be in the form of a dry powder for reconstitution before use, e.g. with sterile, pyrogen-free water. The purine analogs may also be formulated as suppositories utilizing conventional suppository bass such as cocoa butter or other glycerides. The purine analogs may also be formulated into tablets or capsules for oral use.

When provided in unit dosage forms the compositions will preferably contain from about 10 mg to about 100 mg of the purine analog. Although the dosage will depend on such factors as the weight and age of the patient or an animal and is within the discretion of the physician or the veterinarian, the dosage for adult human treatment will usually be in the range of from about 10 mg to about 100 mg per kilogram per day, depending on the frequency and route of administration. When administered intramuscularly or intravenously to an adult human, a total dosage from about 10 mg to 100 mg per kilogram per day, in divided doses, normally will be sufficient, although higher daily doses of some of the purine analogs may be desirable in the case of very severe infections.

The expression African human and veterinary trypanosomiases means a human being or an animal that is infected by the parasite *Trypanosoma brucei brucei*. Such an infection is commonly known as African sleeping sickness and is characterized by 100% mortality if untreated. The animals that are usually infected by this parasite are domestic animals, such as for example, pigs, cattle, sheep, camels, horses, buffaloes, etc.

Having thus generally described the present invention, reference is now made to the following example which illustrates preferred embodiments but which is not to be construed as limiting to the scope of the invention as more broadly setforth hereinabove and in the claims.

EXAMPLE 1

Biological Test Procedures Materials and Methods

Trypansome strains

*T. b. brucei* EATRO 110 isolate was maintained as described (Bacchi, C. J., H. C. Nathan, S. H. Hutner, P. P. McCann and A. Sjoerdsma; Polyamine metabolism: a potential chemotherapeutic target in trypanosomes. *Science* 210: 332–334, 1980). It produces an acute, rapidly fatal parasitemia which is lethal to mice 3–5 days after inoculation. Two *T. B. brucei* strains, TREU 667 and LUMP 1001 developed by Jennings and coworkers (Jennings, F. W., D. D. Whitelaw and G. M. Urquhart; The relationship between duration of infection with *Trypanosoma brucei* in mice and the efficacy of chemotherapy. *Parasitology* 75: 143–153, 1977/Jennings, F. W. and G. D. Gray; Relapsed parasitemia following chemotherapy of chronic *T. brucei* infections in mice and its relation to cerebral trypanosomes; *Contr. Microbiol. Immunol.* 7 147–154, 1983) were used as CNS models. Both produce infections which are refractory to Berenil ® (diminazene aceturate) and develop within 21 days after inoculation. They are not usually fatal until >40 days after inoculation. LUMP 1001 causes a more virulent CNS infection than TREU 667, and is regarded as more difficult to cure (Jennings, F. W. and G. D. Gray. Relapsed parasitemia following chemotherapy of chronic *T. brucei* infections in mice and its relation to cerebral trypanosomes. *Contr. Microbiol. Immunol.* 7 147–154, 1983).

Drug Screen

Swiss-Webster (25–30 g) mice were used throughout. In the EATRO 110 model, groups of 100 mice were infected ($10^5$ trypanosomes/mouse) and the infection was allowed to develop 24 hours before commencing therapy. Animals were divided into groups of 5 before treatment. Cured animals survived >30 days beyond deaths of controls. All compounds were administered by i.p. injection.

The models for control nervous system infections used TREU 667 and LUMP 1001 strains which were stored frozen and passaged once in rats before infection of mice. Maintenance and use of these screens were as described (Clarkson, A. B. Jr., C. J. Bacchi, G. H. Mellon, H. C. Nathan, P. P. McCann and A. Sjoerdsma. Efficacy of DFMO+blemoycin in a mouse model of central nervous system African trypanosomiasis. *Proc. Natl. Acad. Sci. USA.* 80: 5729–5733, 1983/Clarkson, A. B. Jr., E. J. Biene, C. J. Bacchi, P. P. McCann, S. H. Hutner and A. Sjoerdsma. New drug combination for experimental late stage African trypanosomiasis: DFMO with suramin. *Am. J. Trop. Med. Hyg.* 33: 1073–1077, 1984/Dube, D. K., G. Mpimbaza, A. C. Allison, E. Lederer and L. Rovis. Antitrypanosomal activity of sinefungin, *Am. J. Trop. Med. Hyg.* 32: 31–33, 1983/Fish, W. R., J. J. Marr, R. L. Berens, D. L. Looker, D. J. Nelson, S. LaFon and A. E. Balber. Inosine analogs as chemotherapeutic agents for African trypanosomes: metabolism in trypanosomes and efficacy in tissue culture. *Anti-microb. Ag. Chemother.* 27: 33–36, 1985/Clazer, R. I., and L. S. Lloyd. Effects of 8-azaadenosine and formycin on cell lethality and the synthesis and methylation of nucleic acids in human colon carcinoma cells in culture. *Biochem. Pharmacol.* 31: 3207–3214, 1982/Bacchi, C. J., H. C. Nathan, A. B. Clarkson, Jr., E. J. Bienen, A. J. Bitonti, P. P. McCann and A. Sjoerdsma. Activity of the ornithine decarboxylase inhibitors DL-α-difluoromethylornithine and monofluormethyldehydroornithine methylester alone and in combination with suramin against *Trypanosoma brucei brucei* central nervous system models, *Am. J. Trop. Med. Hyg.* (in press)). Briefly, groups of 100–120 mice were infected and the infections allowed to develop until day 21, when the animals were separated into groups of 10 and therapy commenced. Controls were treated with Berenil (40 mg/kg) on day 21. These always relapsed 40–70 days after treatment. Parasitemia was followed by examining tail vein blood smears once weekly. Animals which had relapsed were removed from cages. TREU 667 infections were followed >225 days after inoculation and LUMP 1001 were followed >280 days, as determined by the relapse pattern in previous work (Bacchi, C. J., H. C. Nathan, A. B. Clarkson, Jr., E. J. Bienen, A. J. Bitonti, P. P. McCann and A. Sjoerdsma. Activity of the ornithine decarboxylase inhibitors DL-α-difluoromethylornithine and monofluormethyldehydroornithine methylester alone and in combination with suramin against *Trypanosoma brucei brucei* central nervous system models. *Am. J. Trop. Med. Hyg.* (in press)). "Cured" animals had no evidence of parasitemia and their brain homogenates failed to produce parasitemia >2 weeks after injection into uninfected control animals.

Drugs

9-Deazainosine was synthesized and purified as described (Lim, M-I., W-Y. Ren, B. A. Otter and R. S. Klein. Synthesis of "9-deazainosine" and other new pyrrolo (3, 2-d) pyrimidine C-nucleosides. *J. Org. Chem.* 48: 780–788, 1983. Allopurinol and allopurinol riboside were obtained from Burroughs-Wellcome Co., Research Triangle Park, NC. Sinefungin, Berenil (diminazene aceturate; Calbiochem Biochemicals, San Diego, CA), and formycin B (Sigma Chemical Co., St. Louis, Mo) were purchased.

Analytical Techniques

Animals

Animals (25–30 g) Swiss-Webster mice were purchased from Royal Hart Laboratory Animals, New Hampton, NY.

TABLE 1

Activity of Purine Analogs vs T. b. brucei EATRO 110.
Mice were infected with $10^5$ trypanosomes and the infection allowed to develop 24 h. before treatment was begun. Animals surviving 30 days past death of controls were considered cured. 9-DINO and sinefungin were given by i.p. injection once daily for 3 days.

| Treatment | Dose (mg/kg) | # Cured/Total | % Cured |
|---|---|---|---|
| Allopurinol | 300 | 0/5 | 0 |
| Allopurinol Riboside | 250 | 0/5 | 0 |
| 9-DINO | 400 | 3/5* | 60 |
|  | 200 | 5/5 | 100 |
|  | 100 | 5/5 | 100 |
|  | 50 | 4/5 | 80 |
|  | 25 | 15/20 | 50 |
|  | 10 | 2/30 | 7 |
|  | 5 | 0/5 | 0 |
| Formycin B | 100 | 4/5* | 80 |
|  | 50 | 5/5 | 100 |
|  | 25 | 9/10 | 90 |
|  | 10 | 5/5 | 100 |
|  | 5 | 4/5 | 80 |
|  | 2.5 | 5/5 | 100 |
| Sinefungin | 25 | 4/5 | 80 |
|  | 10 | 8/15 | 53 |
|  | 5 | 9/15 | 60 |
|  | 2.5 | 0/5 | 0 |
|  | 1 | 0/20 | 0 |
|  | 0.5 | 0/15 | 0 |

*Toxic

TABLE 2

Effects of delayed administration of 9-DINO on the EATRO 110 model.
Methods as in Table 1 except 9-DINO administration was begun 48 or 72 h. post infection, and continued for 3 days as single daily injections. Mice with a 48 h. infection had parasitemia levels of 3 to 6 × $10^7$/ml, those with 72 h. infection had 1 to 5 × $10^8$/ml.

| Treatment Begun | Dose (mg/kg) | # Cured/Total | % Cured |
|---|---|---|---|
| 48 h. | 25 | 5/5 | 100 |
|  | 50 | 5/5 | 100 |
|  | 100 | 5/5 | 100 |
| 72 h. | 25 | 6/10* | 60 |
|  | 50 | 6/10* | 60 |
|  | 100 | 6/9* | 67 |

*Only animals receiving full treatment (3 i.p. doses) were included in data tabulation.

TABLE 3

Activity of purine nucleoside analogs on the acute EATRO 110 model infection. Nucleoside analogs were given by i.p. injection once daily for 3 days. Other methods as in Table 1.

| Treatment | Dose | # Cured/Total | % Cured |
|---|---|---|---|
| 9-DINO | 25 mg/kg | 15/20 | 75 |
|  | 10 | 2/30 | 7 |
|  | 5 | 0/5 | 0 |
| Sinefungin | 25 mg/kg | 4/5 | 80 |
|  | 10 | 8/15 | 53 |
|  | 5 | 9/15 | 60 |
|  | 1.0 | 0/20 | 0 |
|  | 0.5 | 0/15 | 0 |
| Formycin B | 0.5 mg/kg | 3/5 | 60 |
|  | 0.25 | 1/10 | 10 |
|  | 0.1 | 0/5 | 0 |
|  | 0.05 | 0/5 | 0 |

TABLE 4

T. b. brucei TREU 667 isolate. Activity of purine nucleoside analogs.
Animals were infected with $10^5$ trypanosomes and the infection allowed to develop for 21 days. Analogs were administered i.p. Animals were checked twice weekly for parasitemia (tail vein blood smears).

| Treatment | Dose | Duration (Days) | Avg. Day of Relapse (Range)* | # Cured/Total | % Cured |
|---|---|---|---|---|---|
| 9-DINO | 250 mg/kg | 7 | 68 (45–86) | 3/10 | 30 |
|  | 100 | 7 | 49 (35–58) | 0/20 | 0 |
|  | 25 | 7 | 60 (41–135) | 1/5 | 20 |
|  | 10 | 7 | 41 | 0/5 | 0 |
|  | 5 | 7 | 41 | 0/5 | 0 |
| Sinefungin | 10 mg/kg | 7 | 124 (35–209) | 6/10 | 60 |
|  | 10 | 3 | 38 (35–46) | 0/10 | 0 |
|  | 5 | 4 | 41 (35–46) | 0/10 | 0 |
|  | 2.5 | 4 | 39 (35–56) | 0/18 | 0 |
| Formycin B | 100 mg/kg | 6 | 35 | 0/9 | 0 |
|  | 50 | 6 | 34 (23–35) | 0/10 | 0 |
|  | 25 | 7 | 40 (37–68) | 0/10 | 0 |
|  | 10 | 7 | 40 (37–41) | 0/9 | 0 |
|  | 5 | 7 | 42 (37–49) | 0/8 | 0 |

TABLE 5

T. b. brucei LUMP 1001 isolate. Activity of 9-DINO. Conditions as in Table 4 and same methods of Table 4.

| Treatment | Dose | Duration (Days) | Avg. Day of Relapse (Range)* | # Cured/Total | % Cured |
|---|---|---|---|---|---|
| 9-DINO | 250 mg/kg | 7 | 49 (35–63) | 0/10 | 0 |
|  | 100 | 7 | 38 (35–44) | 0/9 | 0 |
|  | 50 | 7 | 36 (35–44) | 0/10 | 0 |
| Sinefungin | 10 mg/kg | 3 | 39 (35–71) | 0/10 | 0 |
|  | 5 | 3 | 35 | 0/10 | 0 |
|  | 2.5 | 3 | 35 | 0/10 | 0 |

RESULTS

As can be seen from the tables, several purine analogs were compared for activity in the short term EATRO 110 screen (Table 1). Those having greatest activity were formycin B and 9-DINO. Formycin B was the most active, and was curative over a range of 5–100 mg/kg, although at 100 mg/kg toxicity was observed (20% death rate and loss of hair). 9-DINO was also highly effective, with an active range of 25–200 mg/kg. At 400 mg/kg it was toxic (40% death rate). Comparison of the activity ranges for both compounds indicated that formycin B was >10X more active than 9-DINO (100% cures at 2.5 mg/kg vs 75% cures at 25 mg/kg, respectively). Allopurinol and its riboside were completely inactive at 300 mg/kg. Sinefungin had cured laboratory strains of T. b. brucei, T. congolense and T. vivax (Dube et al., Am. 2. Trop. Med. Hyg., 32: 31–33, 1983) when administered in multiple daily doses, but it was only ~50% effective here in single doses of 5 or 10 mg/kg and 80% active at 25 mg/kg.

9-DINO was also active in the short term model if treatment was delayed 48 or 72 h. post infection (Table 2). At 48 h., mice had a blood parasitemia of 2.5 to $6.2 \times 10^7$/ml. 9-DINO treatment commencing at this time was completely effective at dose ranges of 25 to 100 mg/kg. At 72 h. post infection, mice were clearly ill and had a blood parasitemia of $>1 \times 10^8$/ml. One died within 24 h. Of the animals surviving to receive the complete treatment regimen (3 doses), a 60% cure rate was obtained at 25 and 50 mg/kg and 67% at 100 mg/kg.

9-DINO against the EATRO 110 model in 50–100 mg/kg gave 100% cure rates. Formycin B at 0.5 mg/kg was 60% curative. Purine nucleoside analogs were also tested in two CNS screens. Initial trials were in the TREU 667 model which produces a less virulent CNS infection than the more stringent LUMP 1001 model. In the TREU 667 system (Table 4) none of the analogs were effective. Sinefungin, used at 10 mg/kg×7 doses was 60% curative. Formycin B, used at 100 mg/kg×6 doses was not curative for TREU 667-infected mice.

GENERAL REMARKS

It is known that 9-Deazainosine (9-DINO) a C-C nucleoside analog is converted to toxic adenosine nucleotide analogues by bloodstream trypomastigotes in culture. It is neither toxic for mouse L cells nor metabolized to adenosine nucleotide analogues by these cells, however, it has not been studied in vivo. 9DINO was active against an acute infection. 9-DINO did not cure CNS infections. Previous studies have shown that 9-DINO was more active than allopurinol, thipurinol, and their respective nucleosides against T. cruzi, Leishmania spp and African trypanosomes. The same study also demonstrated that 9-DINO is metabolized to 9-deaza-ATP by T. B. gambiense and T. b. rhodesiense.

Formycin B, another C-C nucleoside derivative, was active against Leishmania spp and T. cruzi in vitro, as well as bloodstream and culture forms of African trypanosomes. Both formycin B and 9-DINO are C-nuceloside purine analogs which cannot be cleaved into ribose and purine analog moieties by mammalian cells. Both compounds can be aminated by T. brucei subsp. and converted to analogs of ATP. A major difference between the two, however, is that formycin B is metabolized by mammalian cells to its aminated analog formycin A which can then be incorporated into nucleic acids. The conversion of formycin B to formycin A of adenine nucleotides in mammalian systems is well known. Mouse L cells can convert formycin B to the analogs of adenine nucleotides and incorporate the ATP analog into RNA. This raises the likely possibility that this can occur in humans. It has been shown that this occurred in human macrophages and that the toxicity of a series of formycin analogs to L. tropica was paralleled by their toxicity for these macrophages. It has been demonstrated that formycin A nucleotides can be incorporated into DNA of human colon carcinoma cells. 9-DINO is not metabolized to adenine nucleotide analogs in mouse L cells and VA-13 human cells, the only systems which have been studied thus far. Although in the short term model, formycin B was more active than 9-DINO (100% cures at 2.5 mg/kg vs 75% cures at 25 mg/kg), in the present experiment toxicity appeared with formycin B at lower doses than with 9DINO (100 mg/kg vs 400 mg/kg: see Table 1).

Sinefungin was less active than 9-DINO and Formycin B in the acute model and did not produce complete cures against CNS models. The low activity is disappointing in light of previous work in which sinefungin cured a chronic strain of *T. congolense* as well as acute *T. b. brucei* and *T. vivax* strains (Dube et al., *Am. 2. Trop. Med. Hyg.*, 32: 31–33, 1983). In this study, sinefungin was administered as multiple daily doses at 2 or 8 h. intervals and at lower total doses than in the present experiment: e.g. the *T. b. brucei* infection was 100% curable with a 3×5 mg/kg dose, administered at 8 hour intervals. *T. congolense* responded to a total dose of 0.45 mg, given as 9 injections 2 h. apart. These findings indicate that there are differences in susceptibility of the strains to sinefungin.

Formycin B was extremely active on the EATRO 110 model. In the TREU 667 (chronic) screen, formycin B failed to protect at 100 mg/kg×6 days.

The above data indicate that 9-DINO is active against acute models of *T. b. brucei*. There is no evidence of toxicity in prolonged (i.e. 1 week) dose regimens and the agent was more effective than sinefungin, allopurinol and allopurinol riboside.

What is claimed is:

1. A method for treating African human and veterinary trypanosomiases, which comprises administering a non-toxic effective amount of 9-deazainosine or its pharmaceutically acceptable acid addition salt thereof, to a human being or an animal in need of such treatment.

2. The method of claim 1, wherein the animal is a pig, cattle, sheep, camel, horse or a buffalo.

3. The method of claim 1, wherein the pharmaceutically acceptable acid salt is a hydrochloride, sulfate or a phosphate.

4. The method of claim 1, wherein the administration is by the parenteral or oral route.

* * * * *